United States Patent [19]

Buechel et al.

[11] Patent Number: 5,030,221
[45] Date of Patent: Jul. 9, 1991

[54] PROSTHESIS HOLDING SYSTEM

[76] Inventors: Frederick F. Buechel, 76 Crest Dr., South Orange, N.J. 07079; Michael J. Pappas, 61 Gould Pl., Caldwell, N.J. 07006

[21] Appl. No.: 450,291

[22] Filed: Dec. 13, 1989

[51] Int. Cl.$^5$ .............................................. A61F 5/04
[52] U.S. Cl. ...................................... 606/91; 606/86; 606/53
[58] Field of Search ................... 606/91, 80; 623/22

[56] References Cited

U.S. PATENT DOCUMENTS

| | | | |
|---|---|---|---|
| 1,766,235 | 6/1930 | Wells | 433/161 |
| 3,859,992 | 1/1975 | Amstutz | 606/91 |
| 4,305,394 | 12/1981 | Bertuch, Jr. | 606/91 |
| 4,475,549 | 10/1984 | Oh | 606/91 |
| 4,486,177 | 12/1984 | Lekawa | 433/161 |
| 4,528,980 | 7/1985 | Kenna | 128/92 |
| 4,716,894 | 1/1988 | Lazzeri et al. | 606/91 |

*Primary Examiner*—Randall Green
*Assistant Examiner*—A. Paul Zutterelli
*Attorney, Agent, or Firm*—Anthony J. Casella; Gerald E. Hespos

[57] ABSTRACT

A prosthesis holding system is provided for holding and positioning a prosthetic cup during surgery. The rim of the cup includes opposed inwardly and outwardly facing recesses. A holder includes an elongated rod having a shoe at one end. The shoe includes a tab for engaging the inwardly facing recess in the rim of the cup. The shoe further includes a threaded aperture alignable with the outwardly facing recess in the rim of the cup. A clamping screw is engageable with the threaded aperture and is further engageable with the outwardly facing recess in the rim of the cup. Tightening of the clamping screw securely holds the cup without interfering with either the interior concave surface of the cup or the exterior convex surface of the cup, to enable efficient implantation of the cup in a patient during surgery.

17 Claims, 2 Drawing Sheets

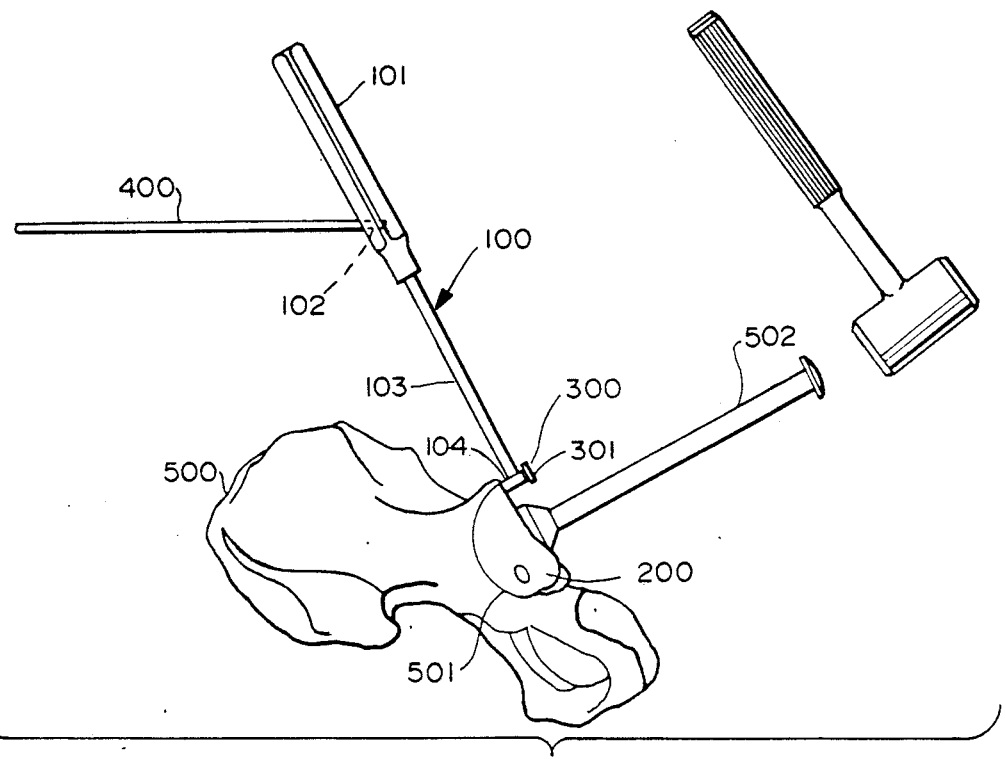
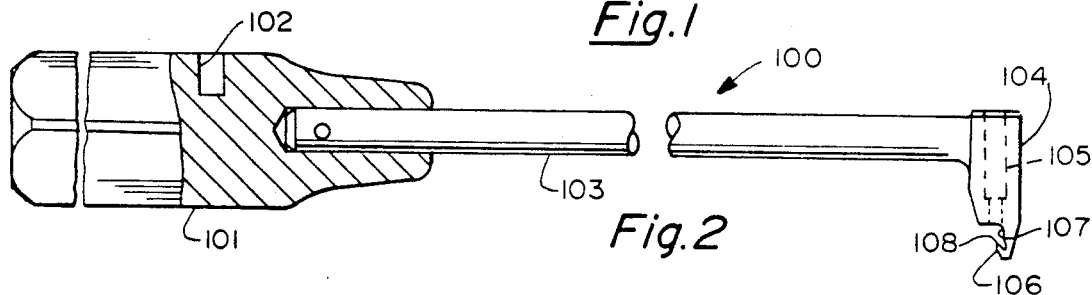
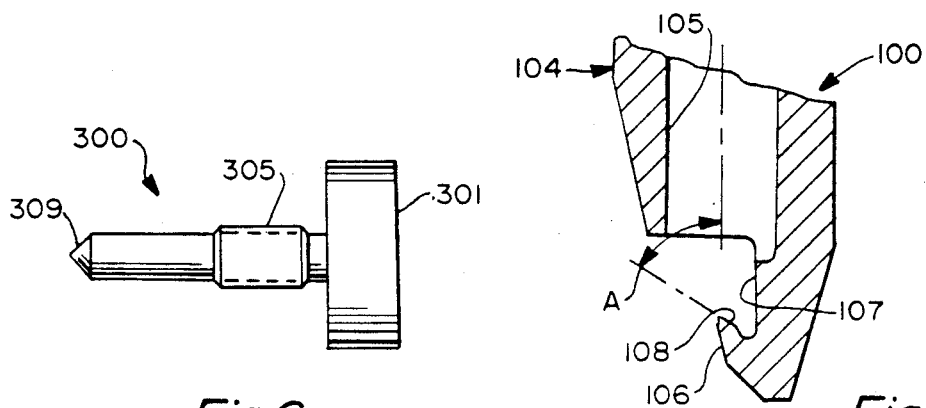

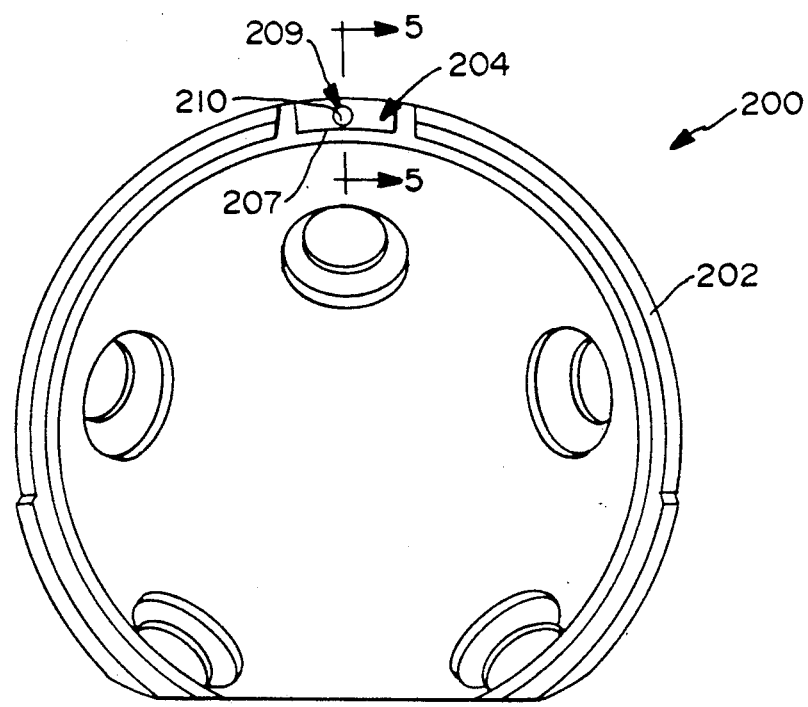
Fig.4
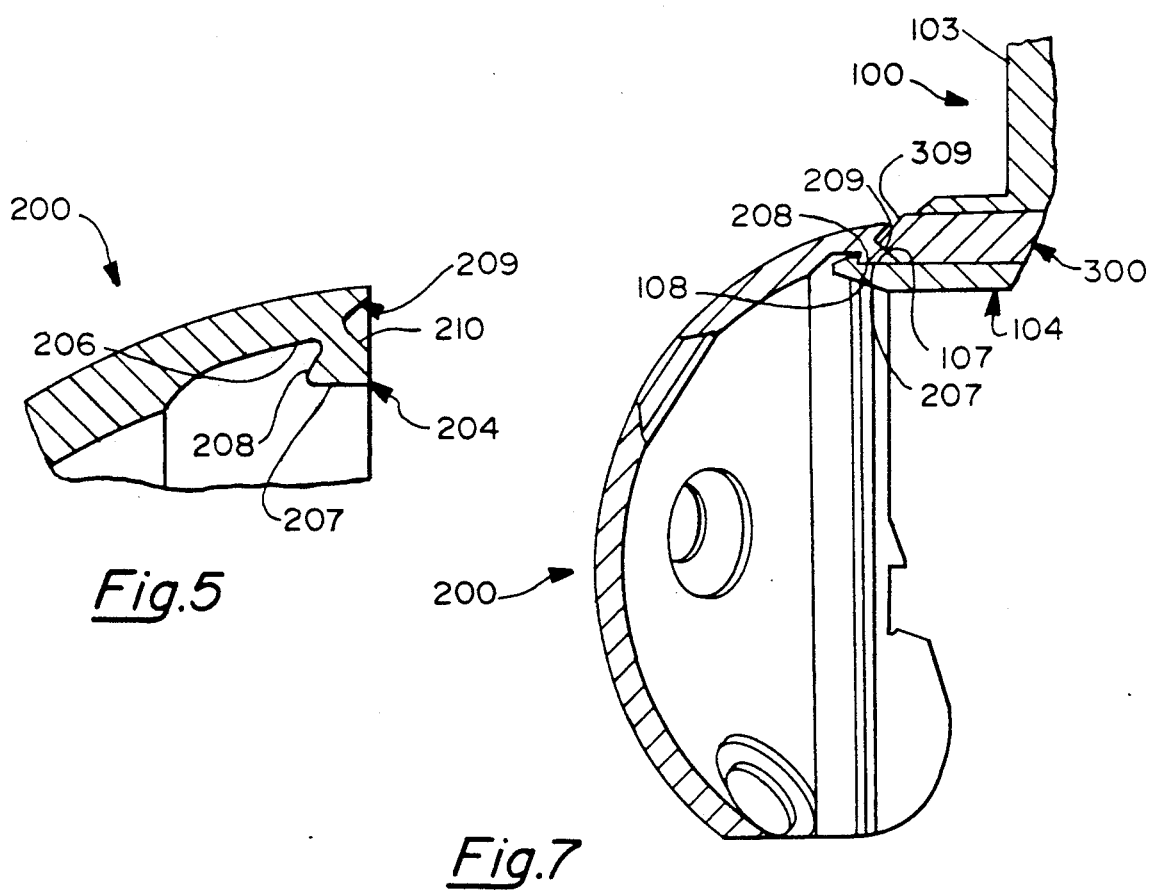
Fig.5
Fig.7

PROSTHESIS HOLDING SYSTEM

BACKGROUND OF THE INVENTION

Surgery to implant prostheses often requires the surgeon to hold and orient an implant during the implantation. Such holding and orientation often is assisted by use of instruments that hold the implant and provide reference surfaces used to position the holder, and therefore the implant which it holds, relative to some body landmarks. Many size implants are employed by the surgeon, hence it would be desirable for the holder to accept all size implants to minimize the number of different instruments needed to hold these different sized implants.

Particularly difficult problems are associated with implanting metal acetabular hip cup shells which are to be fixed to the bone and into which a plastic bearing is inserted. Such cups are typically available in a large number of inside and outside sizes. Current practice is to hold the cup on its inside surface with an instrument that matches the particular size of the surface. Thus most holding instruments are designed with removable holding heads of various sizes. The instrument system needed to hold a large variety of sizes needs to have a large variety of holding heads and is therefore complex.

A further disadvantage of current cup holding methods is that access to the inside surface of the cup is blocked. Although such access is not always needed, there are occasions where such access is desirable. For example, after the acetabular cavity has been prepared and the cup has been positioned, the cup may be impacted in the cavity, and screws may be added to augment the press fit fixation. In many cases, however, defects in the acetabulum make stable, press fit fixation impractical. In such cases it is desirable to hold the cup with the holder while the screws are added. Current cup holders do not allow this option.

The object of this invention is to provide a holding system where one holder can accept all size components in a way which minimizes restriction of access to the surfaces of the implant.

Another object is to provide a holding system where cup impacting tools, screws and screw drivers may be used in the cup while the cup is being held.

A further object of the invention is to provide a holding system which avoids interference with the bone.

SUMMARY OF THE INVENTION

The subject invention is directed to a cup holding system for securely holding and accurately aligning a prosthetic cup during surgery. The cup may be an acetabular cup of a hip prosthesis system. The cup includes a rim having an outwardly or laterally facing engagement means and an opposed inwardly or medially facing engagement means. More particularly, the rim of the cup may include a small positioning projection on which the opposed engagement means are disposed. The engagement means may define recesses on the positioning projection.

The holding system of the subject invention further includes a holder having a holding shoe. The holding shoe includes tab means for engaging the inwardly facing engagement means of the cup. The shoe further includes clamp mounting means for receiving a clamp. The clamp mounting means is disposed to align a clamp with the outwardly facing engagement means of the cup. The clamp mounting means may comprise an aperture, such as a threaded aperture for receiving a screw clamp. The holder may further include a handle disposed to extend away from the cup to avoid impeding access to the cup during surgery.

The system of the subject invention further comprises clamping means engageable with the clamp mounting means of the shoe. The clamping means is selectively moveable into clamping engagement with the outwardly facing engagement means on the cup.

The prosthesis holding system of the subject invention may further include alignment means engageable with at least one selected location on the holder. The alignment means is disposed to enable alignment with a selected landmark on the patient for accurately aligning and positioning the cup.

It will be appreciated that the shoe of the holder and the clamping means engageable therewith are operative to securely grip the cup at a portion of the rim. Thus, the holding means does not interfere with the exterior or convex side of the cup which must be fitted against the patient, nor with the interior or concave surface of the cup which may require access by the surgeon to achieve secure implantation of the cup by impacting means, screws and/or the like. Additionally, it will appreciated that the holder is not dependent upon the geometry of a particular cup. Thus, it is not necessary to provide separate holding tools or a modular set of holding tools to accept cups of varying geometry or dimensions.

BRIEF DESCRIPTION OF THE DRAWINGS

FIG. 1 is a perspective view showing the prosthesis holding system for implanting an acetabular cup into the pelvis of a patient.

FIG. 2 is a side elevational view of the holder of the subject invention.

FIG. 3 is a cross-sectional view of the shoe of the holder depicted in FIG. 2.

FIG. 4 is a front elevational view of an acetabular cup in accordance with the subject invention.

FIG. 5 is a cross-sectional view taken along line 5—5 in FIG. 4.

FIG. 6 is a side elevational view of the clamp screw of the subject invention.

FIG. 7 is a cross-sectional view similar to FIG. 5 but showing the holder engaged with the cup.

DETAILED DESCRIPTION OF THE PREFERRED EMBODIMENT

The prosthesis holding system of the subject invention is illustrated in FIG. 1, and includes a holder 100 for engaging an acetabular cup 200 for intraoperative positioning of the cup 200. The holder 100 is engageable with a clamp screw 300 disposed to securely grip the acetabular cup 200 between portions of the holder 100 and the clamp screw 300 as explained further herein. An alignment rod 400 is engageable with the holder 100 to facilitate alignment of the cup 200 with selected locations on the pelvis 500 or other landmarks on the patient as the cup 200 is being positioned in the acetabular cavity 501.

The acetabular cup holder 100 as shown in FIGS. 2 and 3 consists of a handle 101, in which there are a series of holes 102. A shaft 103 is attached to the handle 101 and a holding shoe 104 is attached to the end of the shaft. The holding shoe 104 contains threaded hole 105 extending orthogonal to the shaft 103. The holding shoe 104 further includes a tab 106 with a lateral face 108, and an orienting surface 107. The orienting surface 107 is substantially parallel to the axis of the threaded hole, while the lateral face 108 is generally in line with the threaded hole 105 and is angularly aligned to the axis of the threaded hole at an angle "A" of about 60° as shown in FIG. 3.

The metal acetabular cup 200 is similar to that described in our co-pending U.S. patent applications Ser. Nos. 712,370 and 205,315, the disclosures of which are incorporated herein by reference. The acetabular cup 200, as shown in FIGS. 4 and 5, includes a rim 202, at least a portion of which is defined by a cutting plane which preferably extends perpendicular to a plane of symmetry through the cup 200. A small projection 204 is defined in the rim 202 of the acetabular cup 200. The projection 204 has: an inferior orientation surface 207, which is complementary to orienting surface 107 on the holder 100; a conical recess 209 with an inferior aspect 210; and a medial recess 206 which accepts the tab 106 of the holder 100. More particularly, this medial recess 206 contains a lateral wall 208, which is dimensioned and angularly aligned to be complementary to the lateral face 108 on the tab 106 of the holder 100.

Turning to FIG. 6, a clamping screw 300 consists of a clamping lever 301, and a threaded shaft 305 with a thread that matches the threaded hole 105 in the acetabular cup holder 100. The clamping screw 300 includes a conical end 309 which is complementary to the conical recess 209 in the acetabular cup 200.

An alignment rod 400 as shown in FIG. 1 fits into one of a series of holes 102 in acetabular cup holder 100.

In use the surgeon engages the holding shoe 104 of acetabular cup holder 100 with projection 204 of acetabular cup 200, such that the tab 106 of the holding shoe 104 fits in the medial or inwardly facing recess 206 of the acetabular cup 200, as shown in FIGS. 1 and 7. The surgeon then turns the clamping screw 300 by means of the clamping lever 301 until the conical end 309 of the clamping screw 300 engages the inferior aspect 210 of the conical recess 209 in the projection 204 of the acetabular cup 200. Further turning of the clamping screw 300 causes the lateral face 108 of the tab 106 of the shoe 104 of the acetabular cup holder 100 to engage the lateral wall 208 of the medial recess 206 in the projection 204 of the acetabular cup 200. If the orienting surface 107 of the holding shoe 104 does not initially engage the inferior orientation surface 207 of the projection, additional turning of the screw 300 will cause the conical end 309 thereof to slide on the inferior aspect 210 of the conical recess 209 and will further cause the lateral face 108 of the holding shoe 104 to slide on the lateral wall 208 of the projection 204 of the acetabular cup 200 until the orienting surface 107 of the holding shoe 104 does engage inferior orientation surface 207 of the cup projection 104. Further turning of the clamp screw 300 will cause simultaneous engagement and tight clamping of: (1) the orienting surface 107 of the shoe 104 with the inferior orientation surface 207 of the acetabular cup 200; (2) the conical end 309 of the clamping screw 300 with the inferior aspect 210 of the conical recess 209 of the acetabular cup 200; and, (3) the lateral face 108 of the shoe 104 with the lateral wall 208 of the acetabular cup 200. Thus, this turning of clamping screw 300 firmly and positively holds acetabular cup 200 to acetabular cup holder 100. The surgeon then inserts the alignment rod 400 in one of the series of holes 102, selecting the hole 102 corresponding to the landmark of the patient and cup orientation the surgeon desires. The acetabular cup 200 with the holder 100 attached is then placed in the acetabular cavity 501 of the pelvis 500 as shown in FIG. 1, the alignment rod 400 is used to help establish proper acetabular cup 200 orientation. In this orientation, the shoe 104 is disposed to avoid interference with the interior of the cup 200, and the handle 101 and shaft 103 are directed away from the cup 200. The acetabular cup 200 is then impacted into acetabular cavity 501 by acetabular impactor 502. Fixation screws may be installed if needed before or after releasing clamping screw 300 and removing the acetabular cup holder 100.

We claim:

1. A prosthetic cup holder assembly for securely positioning a prosthetic cup, said cup including an interior concave surface, an exterior convex surface and a rim extending therebetween, a portion of said rim being configured to define an inwardly facing engagement means and an opposed outwardly facing engagement means, said holder assembly comprising:

a holder having a tab means dimensioned and disposed for engaging the inwardly facing engagement means of the cup and a clamp mounting means spaced from the tab means of the holder; and a clamp means engageable with the clamp mounting means of the holder for clamping engagement with the outwardly facing engagement means of the cup, whereby upon engagement of the tab means of the holder with the inwardly facing engagement means of the cup, the clamp means can be clamped into tight clamping engagement with the outwardly facing engagement means of the cup, for securely engaging the cup with the holder.

2. An assembly as in claim 1 wherein the inwardly facing engagement means of the cup defines a recess, and wherein the tab means of the holder is configured to be moved into tight clamped engagement with the inwardly facing recess of the cup in response to clamping forces generated by the clamp means.

3. An assembly as in claim 1 wherein the outwardly facing engagement means of the cup defines a recess, and wherein the clamp is engageable with the outwardly facing recess of the cup.

4. An assembly as in claim 3 wherein the outwardly facing recess of the cup is substantially conical, and wherein the clamp means comprises a conical end portion substantially corresponding to the shape of the conical recess in the cup.

5. An assembly as in claim 4 wherein the clamp means comprises a clamping screw having opposed axial ends, the conical portion of the clamping screw being disposed at one axial end thereof, the clamp mounting means of the holder comprising a threaded aperture for engaging the clamping screw.

6. An assembly as in claim 1 wherein the holder further comprises an elongated handle extending from portions of the holder having the tab and the clamp mounting means, said handle being disposed to extend away from the cup.

7. An assembly as in claim 6 wherein the handle is provided with at least one aperture disposed therein, and wherein the assembly further comprises at least one alignment rod selectively engageable in the aperture of the handle.

8. A system for holding a prosthetic device during surgery, said system comprising:

a prosthetic cup having an inner concave surface, an outer convex surface and a rim extending therebetween, a portion of said rim defining a projection having an inwardly facing recess and an outwardly facing engagement means;

a holder comprising a holding shoe having a tab for engaging the inwardly facing recess of the cup and clamp mounting means disposed on the shoe at a location thereon spaced from the tab; and, a clamp engageable with the clamp mounting means in the shoe of the holder, said clamp comprising an end portion configured to engage the outwardly facing engagement means of the cup, whereby the cup is securely clampable between the tab of the holder shoe and the end of the clamp.

9. A system as in claim 1 wherein the outwardly facing engagement means of the cup is substantially conical, and wherein the end of the clamp defines a conical shape substantially conforming to the conical engagement means of the cup.

10. A system as in claim 9 wherein the conical engagement means of the cup defines a conical recess, and wherein the conical end of the clamp defines a conical point for engaging the conical recess of the cup.

11. A system as in claim 10 wherein the clamp mounting means of the shoe defines a threaded aperture, and wherein the clamp defines a clamping screw threadedly engageable with the threaded aperture of the shoe.

12. A system as in claim 8 wherein the holder further comprises an elongated handle extending from the shoe thereof.

13. A system as in claim 12 wherein the handle is disposed to extend away from the cup upon engagement of the shoe and the clamp with the cup.

14. A system as in claim 12 wherein the handle comprises at least one aperture formed therein, and wherein said system further comprises an alignment rod selectively engageable in the aperture for aligning the handle with a selected portion of a patient.

15. A system as in claim 8 wherein the cup further includes an orienting surface disposed on the projection generally intermediate the inwardly facing recess and the outwardly facing engagement means, and wherein the holder comprises an orienting surface disposed intermediate the tab and the clamp mounting means thereof for engaging the orienting surface of the cup.

16. A system as in claim 15 wherein the orienting surface on the projection of the cup defines an inferiorly facing surface, the inwardly facing recess being disposed to define a medially facing recess having a lateral wall angularly aligned to the orienting surface of the projection, and wherein the outwardly facing engagement means defines a laterally opening conical recess having an inferior aspect angularly aligned to the orienting surface of the projection, the tab of the holding shoe including an orienting surface for engaging the orienting surface of the cup, the tab of the holding shoe further including a lateral face angularly aligned to the orienting surface of the holding shoe for engaging the lateral wall of the medially facing recess in the cup, said clamp comprising a conical tip for engaging the inferior aspect of the conical recess in the cup, such that the lateral wall, the orienting surface of the projection and the inferior aspect of the conical recess are clampingly engaged respectively by the lateral face of the tab, the orienting surface of the holding shoe and the conical tip of the clamp.

17. An assembly for holding an acetabular cup during surgery, said cup including a medially facing convex surface, a laterally opening concave surface and a rim extending between the concave and convex surfaces, said rim being defined by at least one generally planar cutting plane and including a projection at a superior region of said cup, said projection including an inferior orienting surface, a medial recess having a lateral wall aligned to said orienting surface at an acute angle, and a laterally opening conical recess having an inferior aspect, said assembly comprising:

a holding shoe having an orienting surface generally conforming to the shape of the orienting surface on the cup, a tab having a lateral face aligned to the orienting surface of the holding shoe at an angle substantially corresponding to the angular alignment between the orienting surface and lateral wall of the cup and a threaded aperture extending through said shoe generally parallel to the orienting surface thereof;

a clamping screw threadedly engageable with the threaded aperture in the holding shoe, said clamping screw including a conical tip for engagement with the conical recess in the cup; and a handle rigidly extending from the holding shoe, said handle being aligned with respect to the orienting surface of the holding shoe to substantially avoid interference between the handle and the cup during surgery.

* * * * *